United States Patent [19]

Wheatley et al.

[11] Patent Number: 5,258,436
[45] Date of Patent: Nov. 2, 1993

[54] FILM-FORMING COMPOSITION; METHOD OF PRODUCING SAME AND USE FOR COATING PHARMACEUTICALS AND FOODS AND THE LIKE

[75] Inventors: Thomas A. Wheatley, Richboro, Pa.; Clayton I. Bridges, Jr., Somerset; Carl R. Steuernagel, Medford, both of N.J.

[73] Assignee: FMC Corporation, Philadelphia, Pa.

[21] Appl. No.: 764,027

[22] Filed: Sep. 23, 1991

Related U.S. Application Data

[63] Continuation-in-part of Ser. No. 452,896, Dec. 19, 1989, abandoned.

[51] Int. Cl.⁵ .................................................. C08K 5/05
[52] U.S. Cl. .................................. 524/388; 524/386; 424/474; 424/475; 424/476; 424/481; 424/482; 424/439; 424/479; 424/480
[58] Field of Search .................. 524/386, 388; 424/474, 424/475, 476, 481, 482, 439, 479, 480

[56] References Cited

U.S. PATENT DOCUMENTS

| | | | |
|---|---|---|---|
| 3,981,984 | 9/1976 | Signorino | 524/379 |
| 4,138,013 | 2/1979 | Okajima | 524/24 |
| 4,330,338 | 5/1982 | Banker | 524/388 |
| 4,683,256 | 7/1987 | Porter et al. | 524/285 |
| 4,816,298 | 3/1989 | Alderman et al. | 106/189 |
| 4,960,814 | 10/1990 | Wu et al. | 524/311 |
| 4,968,350 | 11/1990 | Bindschaedler et al. | 523/334 |

*Primary Examiner*—Paul R. Michl
*Assistant Examiner*—Edward Cain
*Attorney, Agent, or Firm*—Robert D. Jackson; Patrick C. Baker

[57] ABSTRACT

A water dispersible polymeric film-forming particulate composition for use in coating pharmaceuticals and foods or the like, produced by freeze-drying an aqueous solution of water-soluble cellulose acetate as the film-forming polymer, a plasticizer, and optionally a pigment, is described. The product mixes readily with water to form an aqueous dispersion which is applied in the conventional manner to solid pharmaceutical forms.

10 Claims, No Drawings

FILM-FORMING COMPOSITION; METHOD OF PRODUCING SAME AND USE FOR COATING PHARMACEUTICALS AND FOODS AND THE LIKE

This is a continuation-in-part of our U.S. patent application Ser. No. 452,896, filed on Dec. 19, 1989 abandoned.

FIELD OF THE INVENTION

This invention relates to solid film-forming compositions for use in coating foods and pharmaceuticals and the like. More particularly, the invention is concerned with such film-forming compositions which are dispersible in aqueous media.

BACKGROUND OF THE INVENTION

It is well known in the art to envelop solid pharmaceutical materials, tablets, granules and seeds, for example, in a film covering as protection against oxidation, moisture, light, abrasion, rough handling, etc. The film should be free of roughness, irregularities, cracks or mottled colorations. Film smoothness is important as an aid in swallowing. A hard, shiny surface is desirable for an attractive appearance. Of course, films and coating compositions for ingestion must be edible or physiologically compatible.

Film-forming compositions for coating pharmaceutical tablets preferably contain as the film-forming element, a film-forming resinous material, either naturally occurring or synthetic. Normally, such compositions are applied as a liquid coating formulation comprising a liquid carrier medium having dispersed or dissolved therein the film-forming components. The liquid medium can be an organic solvent or water or a combination of both. Water is preferred owing to the risk of fire and toxicity from organic solvents. Also having to comply with governmental safety standards pertaining to the transportation and handling of industrial chemicals is another minus factor against solvent use.

Generally speaking, application of the liquid coating formulation is effected by spraying dry pharmaceutical forms in rotation in a coating pan or in a fluidized air bed. After evaporation of the liquid medium, the film coated pharmaceuticals are recovered.

As a commercial product, liquid coating compositions are unsatisfactory because of the high transportation costs due to the weight of the liquid carrier. Clearly, it is more practical and economical to ship coating compositions in dry form which can be reconstituted with the appropriate solvent or liquid by the pharmaceutical customer. For this, a readily dispersible product is desirable which can be reconstituted by simple mixing or stirring.

It is known in the prior art to prepare dry coating formulations by grinding a polymer powder with pigment particles and grinding the mixture further to give a fine powder. However, when this is stirred into water, the polymer tends to agglomerate resulting in a nonuniform dispersion which, unless permitted to solvate for an extended period of time, gives poor coatings due to the presence of lumps and fish eyes.

An improved coating system is described in U.S. Pat. Nos. 4,543,370 and 4,683,256 assigned to the Colorcon Corporation. According to these documents, a pharmaceutical coating composition is produced by high intensity blending of polymer and pigment particles in the presence of a plasticizer. The resulting powder is mixed with water to form a coating dispersion which is applied to tablets. On drying a uniform film is said to be produced on the tablets. The coating can also be applied as a solution in an organic solvent.

The dry coating compositions of the Colorcon patents consist of separate individual particles of pigment and polymer. Although the vigorous dry blending produces a fine powder, its heterogeneous nature is readily discernible under the scanning electron microscope.

SUMMARY OF THE INVENTION

A technique has now been found whereby solid, water dispersible film-forming compositions which are of a homogeneous nature can be realized and the provisions and preparation of said compositions together with film coated pharmaceuticals and the like prepared therewith constitutes the object and purpose of the invention.

The solid water dispersible film-forming compositions of the invention comprise freeze-dried particles of a film-forming water-soluble cellulose acetate (WSCA) produced by freeze-frying an aqueous solution of the polymer. Normally, the WSCA polymer solution will contain a plasticizer and pigment which subsequently appear homogeneously distributed in each of the freeze-dried particles derived from the polymer solution. On mixing the homogeneous film-forming composition with water, there is produced an aqueous film-forming coating dispersion comprising a solution of the WSCA in which are suspended any particulates such as pigments, colorants or the like. As understood herein, the term "dispersion" includes the aqueous polymer solution alone or in combination with suspended matter. The aqueous coating dispersion can be applied to various articles such as a pharmaceutical or food substrate. After drying, there remains a smooth homogeneous film envelope on the so-coated object.

The WSCA aqueous dispersions of the invention, prepared from the freeze-dried WSCA, does not separate upon standing overnight being superior in this respect to the aqueous dispersions formed from the dry blended polymer compositions of the aforecited U.S. Pat. Nos. 4,543,370 and 4,683,256.

DETAILED DESCRIPTION OF THE INVENTION

In carrying out the invention, there is first prepared an aqueous solution of WSCA to which is added plasticizer and optionally a pigment. After thoroughly blending the ingredients a homogeneous liquid is produced. This generally contains a solids content of from about 5% to about 40%, preferably about 10% to about 20%. Of the solids, about 50% to about 90%, preferably about 80% to about 90% is polymer; about 2% to about 40%, preferably about 5% to about 10% is plasticizer and about 0% to about 20%, preferably about 5% to about 7.5% is pigment; all percentages are on a 100% by weight basis.

The so prepared polymer solution is subjected to freeze-drying. In the procedure employed herein, the polymer solution is frozen in bulk by placing it in large trays followed by crushing or pulverizing of the resultant frozen mass to the desired particle size. The frozen WSCA particles are then dried under vacuum with controlled heat to remove moisture and thereby produce dried polymer particles. Freeze-drying is a well known industrial technique for removing water and moisture from an aqueous substrate; see Chemical and Process Technology Encyclopedia by Douglas M. Considine, Editor-in-Chief; McGraw-Hill Book Company, pages 523-527.

The freeze-dried (lyophilized) pulverulent film-forming composition of the invention consists mainly of highly porous, sponge-like particles having a bulk density of the order of about 100 mg/ml to 400 mg/ml. However, particle size is not critical except insofar as it affects the rate of dispersion, larger particles requiring a longer time to undergo dispersion than smaller particles.

The lyophilized powder in the above produced particle sizes is dispersed in water, using ordinary mixing or agitation means, such as a variable speed propeller mixer, to give an aqueous, film-forming coating composition. Mixing time to obtain a homogeneous dispersion is of the order of about 15 to about 30 minutes. Exemplary particle size ranges from about 75 to 850 microns, preferably, about 60 to 250 microns.

Viscosity of the dispersion is a function of polymer, concentration and molecular weight. By varying these parameters, dispersions having a wide range of viscosities can be realized. Viscosities (Brookfield RVT, Spindle #3 at 20 rpm) of the film-forming dispersions of the invention are typically in the neighborhood of 300 to 700 cps. The compositions are stable and do not settle out or agglomerate over a 24 hour period.

Microscopic examination of the freeze-dried particles of WSCA reveals their homogeneous nature; none of the individual components making up the particle can be discerned. It is believed that this homogeneity at the particle level accounts for superior suspension stability of the dispersion and improved smoothness of the film coatings as compared with film coatings made from dry blends of polymer and pigment. Tests on pharmaceutical forms coated with the pigmented polymer showed excellent preservation of cores against heat and humidity.

WSCA is a known material which is extensively documented in the patent and technical literature; see for instance, U.S. Pat. No. 3,482,011 to Bohrer and assigned to Celanese Corporation. The polymer is available in various viscosity grades from the Hoechst-Celanese Corporation, Charlotte, N.C. 28232. Films obtained with water-soluble cellulose acetate are clear, flexible, strong and durable.

WSCA employed herein is preferably a mixture of low and medium viscosity types to provide a polymer blend from which aqueous polymer dispersion can be prepared having the aforementioned viscosity in the 300 to 700 cps. range.

Any of the pigments commonly used in making coating dispersions for coating tablets and the like are suitable for inclusion in the dry film-forming compositions of the invention. Examples are FD&C and D&C lakes, titanium dioxide, magnesium carbonate, talc, pyrogenic silica, iron oxides, channel black and insoluble dyes. Also satisfactory are natural pigments such as riboflavin, carmine 40, curcumin and annatto; pigments are optional ingredients which can be omitted.

Plasticizers for the WSCA in the coatings of the invention include polyethylene glycols (PEG) having a molecular weight range of about 200 to 4000, acetylated monoglyceride, glycerin, propylene glycol, triethyl citrate, acetyl triethyl citrate, triacetin; preferred plasticizers are glycerin and PEG 400.

The film-forming composition can be used to coat pharmaceuticals such as tablets, seeds, granules, pellets, soft and hard gelatin capsules and the like.

The aforementioned pharmaceutical dosage forms comprise drug classes such as multivitamins, multivitamins with minerals, prenatal vitamins, vitamins A and D, $B_1$, $B_2$, $B_6$, $B_{12}$, and vitamin B complex with vitamin C. Additional drug classes include:

Analgesics—acetaminophen, aspirin, ibuprofen, ketoprofen and the like, indomethacin, naproxen, acetaminophen with codeine and acetaminophen with propoxyphene napsylate.

Antibiotics—erythromycin, cephalosporins, etc.

Antiepileptics—phensuximide, phenytoin sodium and valproate sodium.

Antihistamines—chloropheniramine maleate, diphenhydramine hydrochloride, triprolidine hydrochloride, etc.

Cough and Cold Drugs—dextromethorphan hydrobromide, ephedrine sulfate, quaifenesin, phenylpropanolamine hydrochloride, promethazine hydrochloride, and pseudoephedrine hydrochloride.

Cardiovascular Drugs—captopril, chlorthiazide and hydrochlorthiazide, diltiazem, nadolol, papaverine hydrochloride, procainamide hydrochloride, propranolol hydrochloride, quinidine gluconate, quinidine sulfate, etc.

Electrolytes—potassium chloride.

Gastrointestinal Drugs—cimetidine, loperamide hydrochloride and ranitidine.

Respiratory Drugs—albuterol sulfate, aminophylline, theophylline, etc.

The following nonlimiting examples in which all parts are by weight unless otherwise stated, illustrate the invention.

EXAMPLE 1

Dry Film-Forming Coating Powder (A) Formula

| Components | Composition Suspension | Solids | % |
|---|---|---|---|
| WSCA*, low viscosity (15%) | 2963.0 | 444.5 | 59.3 |
| WSCA, medium viscosity (10%) | 2222.3 | 222.2 | 29.6 |
| PEG 400 | 33.3 | 33.3 | 4.4 |
| Sepisperse ®, AP3027** | 190.2 | 50.0 | 6.7 |
| Water | 591.2 | — | — |
|  | 6000.0 g | 750.0 g | 100.0 |

*Water-soluble cellulose acetate
**Sepisperse ® AP3027 is a commercial aqueous pigment dispersion manufactured by Seppic, Paris, France. It contains 26.3% by weight pigment solids and 7.5% pigment solids were used based on total polymer solids.

(B) Preparation

1. Low viscosity LV (15% by weight) and medium viscosity MV (10% by weight) water-soluble cellulose acetate (WSCA) solutions are prepared separately.
2. The solutions are mixed (standard variable speed propellor-type mixer) for 60 to 120 minutes, covered and allowed to stand overnight to ensure complete hydration of the polymer.
3. Appropriate amounts of each polymer solution are combined and mixed to achieve the desired polymer ratio. In the case of this example, the polymer ratio of LV:MV is 2:1.

4. With continued mixing, water-soluble PEG 400 is added to the LV:MV WSCA polymer solution.

5. With continued mixing, Sepisperse^R aqueous pigment dispersion is added to the plasticized polymer solution.

6. Water is added to the suspension to adjust the solids in the final composition to 12.5% by weight and the composition is mixed thoroughly.

7. The composition is then lyophilized by conventional freeze drying process.

(C) Film-Forming Coating Dispersion

The above obtained freeze-dried product (in powder form) can easily be redispersed in water to form a composition suitable for coating tablets and the like.

Procedure for dispersing (mixing) the freeze-dried powder is as follows:

1. With a variable speed propellor-type mixer, freeze-dried powder is added to water and mixed for 15 to 30 minutes to form a uniform dispersion.

2. In the case of this example, the concentration of solids in the coating dispersion is 12.5% by weight.

3. Following conventional tablet coating procedures as described below, the dispersion from step 2. is applied to standard acetylsalicylic acid (ASA) tablets at a film loading of 3% based on the coated tablet weight.

| Spray Coating Equipment | |
| --- | --- |
| Pan | 24" Accela-Cota |
| Baffles | 4 straight & 4 mixing |
| Pump | Masterflex 7562-10 |
| Pump heads | Two 7015 |
| Spray guns | Two SS 7310-¼JAU |
| Fluid caps | 1.0 mm |
| Air caps | 134255-45° SS |
| Spray Coating Conditions | Range |
| Batch size (kg) | 10 |
| Spray rate (ml/min/gun) | 15–16 |
| Atomizing air (Bar) | 1.5 |
| Gun distance (inches) | 6 at 45° |
| Air temperature (°C.) | |
| Inlet | 60–75 |
| Exhaust | 36–40 |
| Bed temperature (°C.) | 32–35 |
| Pan rotation (rpm) | 10 |
| Tablet bed warming (min. jogging) | 10 |
| Total coating time (min.) | 65–80 |
| Post drying | |
| Inlet air temperature (°C.) | 60 |
| Drying time (min.) | 20 |
| Tablet weight gain (wt/wt %) | 2.7–3.0 |

EXAMPLE 2

The procedure of Example 1 was repeated except that glycerin was used as the plasticizer. Comparable results were obtained.

We claim:

1. A dry solid polymeric film-forming particulate composition for use in coating pharmaceutical and foods or the like comprising water-soluble cellulose acetate as the film-forming polymer having incorporated therein, a plasticizer and optional pigment produced by freeze drying an aqueous solution of the water-soluble cellulose acetate in which the total solids content of the solution is from about 5% to about 40%, the solids containing about 50% to about 90% polymer, about 2% to about 40% plasticizer selected from the group consisting of polyethylene glycol of molecular weight range of about 200 to about 4000; triethyl citrate, acetyl triethyl citrate, triacetin and glycerin and about 0% to about 20% pigment the said film-forming composition being capable of dispersal in an aqueous medium to give a water based liquid coating composition.

2. The composition of claim 1 wherein the plasticizer is glycerin.

3. The composition of claim 1 wherein the plasticizer is polyethylene glycol of molecular weight 400.

4. The composition of claim 1 wherein the viscosity (Brookfield RVT Spindle #3 at 20 rpm) of the water-soluble cellulose acetate is from about 300 to 700 cps.

5. A dry, film-forming particulate composition for use in coating pharmaceuticals and foods or the like comprising a film-forming water-soluble cellulose acetate having a viscosity (Brookfield RVT Spindle #3 at 20 rpm) of about 300 to about 700 cps., having incorporated therein a plasticizer selected from the group consisting of glycerin and a polyethylene glycol having a molecular weight of from about 200 to about 4000 and a pigment, the said dry, film-forming particulate composition being produced by freeze-drying an aqueous solution containing about 80% to about 90% of the water-soluble cellulose acetate; from about 5% to about 10% of the plasticizer and from about 5% to about 7.5% of the pigment and being capable of dispersal in an aqueous medium to give a water based liquid coating composition.

6. A process for enveloping pharmaceuticals and food products or the like in a protective film comprising the steps of:

forming an aqueous dispersion of a dry solid film-forming particulate composition containing water-soluble cellulose acetate as the film-forming polymer having incorporated therein a plasticizer selected from the group consisting of polyethylene glycol of molecular weight range of about 200 to about 4000; triethyl citrate, acetyl triethyl citrate, triacetin and glycering and optional pigment, the total solids content of the aqueous polymer solution being about 5% to about 40%, the solids containing about 50% to about 90% polymer; about 2% to about 40% plasticizer and about 0% to about 20% pigment, and being produced by freeze-drying, and aqueous solution of the water-soluble polymer containing the plasticizer and pigment, and spraying said dispersion on the form to be enveloped.

7. The process of claim 6 wherein the plasticizer is selected from the class consisting of glycerin and polyethylene glycol having a molecular weight of from about 200 to about 4000.

8. A process for enveloping pharmaceuticals and food products or the like in a protective film comprising the steps of:

forming an aqueous dispersion of a dry solid film-forming composition having a solids content of from about 10% to about 20% comprising from about 80% to about 90% of a film-forming water-soluble cellulose acetate; from about 5% to about 10% of a plasticizer selected from the group consisting of polyethylene glycol of molecular weight range of about 200 to about 4000; triethyl citrate, acetyl triethyl citrate, triacetin and glycerin, and from about 5% to about 7.5% of a pigment, and being produced by freeze-drying an aqueous solution of the water-soluble cellulose acetate containing the plasticizer and pigment, and spraying said dispersion on the form to be enveloped.

9. The process of claim 8 wherein the plasticizer is selected from the class consisting of glycerin and a polyethylene glycol having a molecular weight of from about 200 to about 4000.

10. The process of claim 9 wherein the pigment is mixture of TiO$_2$ and yellow iron oxide in the following formulation:

|  | Wt. Percent |
|---|---|
| Propylene Glycol | 44.0 |
| Water | 26.7 |
| HPMC | 3.0 |
| Pigment Solids | 26.3 |
|  | 100.0% |

* * * * *